United States Patent
O'Rourke

(10) Patent No.: US 10,064,715 B2
(45) Date of Patent: Sep. 4, 2018

(54) METHOD AND DEVICE FOR TREATING A STIFFENED BLOOD VESSEL

(75) Inventor: Michael O'Rourke, Hunters Hill (AU)

(73) Assignee: Aortic Wrap Pty Ltd, Darlinghurst (AU)

( * ) Notice: Subject to any disclaimer, the term of this patent is extended or adjusted under 35 U.S.C. 154(b) by 376 days.

(21) Appl. No.: 13/594,234

(22) Filed: Aug. 24, 2012

(65) Prior Publication Data

US 2013/0226280 A1    Aug. 29, 2013

(51) Int. Cl.
*A61F 2/06*    (2013.01)

(52) U.S. Cl.
CPC ...................... *A61F 2/06* (2013.01)

(58) Field of Classification Search
CPC ........................................... A61F 2/06
USPC .................. 623/1.15; 606/153, 158; 604/507
See application file for complete search history.

(56) References Cited

U.S. PATENT DOCUMENTS

| 6,808,484 B1 * | 10/2004 | Peters et al. ..................... 600/18 |
| 2007/0027528 A1 * | 2/2007 | Agnew ................. A61F 2/2412 623/1.24 |
| 2008/0183280 A1 * | 7/2008 | Agnew ................. A61F 2/2418 623/1.24 |

FOREIGN PATENT DOCUMENTS

| AU | 2012216373 A1 | 3/2013 |
| WO | 2004/056274 A1 | 7/2004 |

* cited by examiner

*Primary Examiner* — Matthew Schall
(74) *Attorney, Agent, or Firm* — Kilpatrick Townsend & Stockton, LLP

(57) ABSTRACT

A device (100) for treating a stiffened blood vessel comprises a self-supporting, surgically implantable, elongate casing (101) adapted to extend about and restrain a stiffened portion (2) of the blood vessel. The casing (101) defines an elongate cavity (103) for receipt of the stiffened portion (2) of the blood vessel. The cavity (103) has a transverse cross-section with an aspect ratio of greater than one in an unloaded state. The casing (103) is configured such that, upon application of increasing pressure to the casing (101) from within said cavity (103), the casing (103) elastically deforms such that the aspect ratio decreases towards one and the area of the cross-section increases.

9 Claims, 7 Drawing Sheets

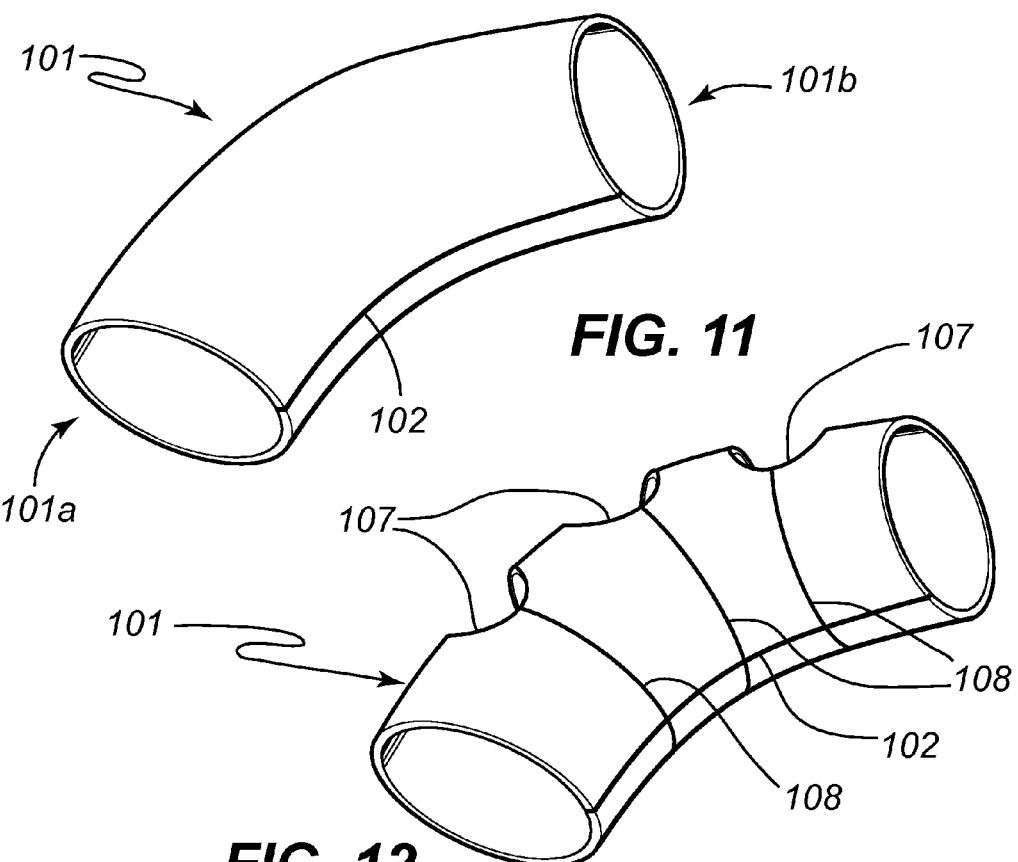
FIG. 11
FIG. 12
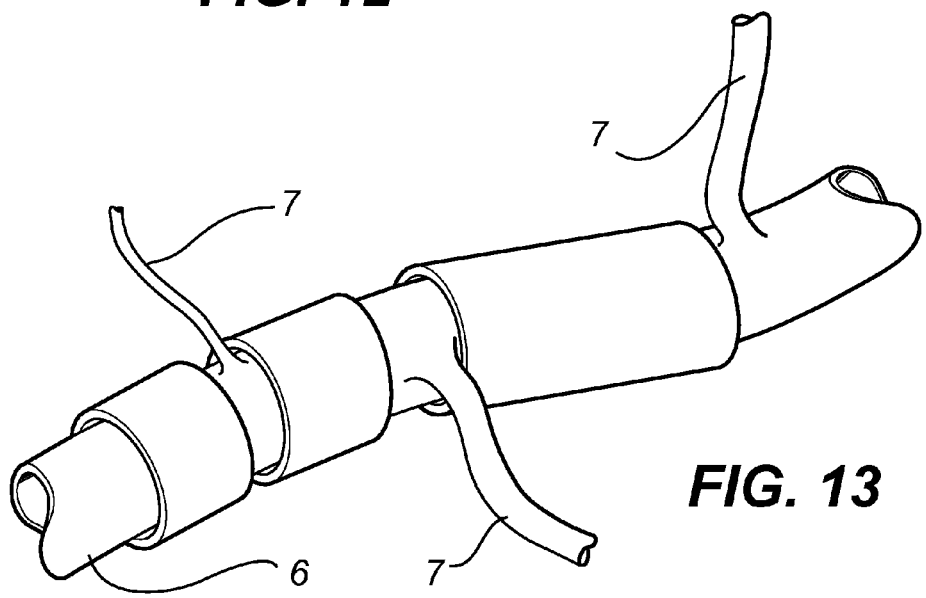
FIG. 13

METHOD AND DEVICE FOR TREATING A STIFFENED BLOOD VESSEL

CROSS REFERENCE TO RELATED APPLICATION DATA

The present application claims the benefit under 35 USC 119(a) of Australian Appln. No. 2011903473 filed Aug. 29, 2011. The full disclosure of which is incorporated herein by reference in its entirety for all purposes.

TECHNICAL FIELD

The present invention relates to the treatment of a stiffened blood vessel, and in particular relates to, but is not limited to, a method and device for treating a stiffened and dilated artery to reduce cardiac load and increase coronary perfusion.

BACKGROUND OF THE INVENTION

The left ventricle of the heart pumps cyclically to deliver oxygenated blood to the body via the aorta. The cyclic pumping of the left ventricle of the heart includes a systole stage and a diastole stage, depicted in FIGS. 1 and 2 respectively.

During the systole stage, the left ventricle 1 contracts, pumping blood to the aorta 2 through the aortic valve 3. Contraction of the left ventricle 1 increases the pressure in the aorta 2, causing the aorta 2 to expand, as depicted in FIG. 1 and as a continuous line in FIG. 3. The expansion absorbs some of the shock loading associated with ejection of blood from the left ventricle. At various points 4 along the aorta, the aorta wall may be subject to anatomical constraints restricting the ability of the aorta to expand. The systolic blood pressure is the maximum blood pressure in the aorta during the systole stage.

During the diastole stage, the left ventricle 1 relaxes and the aortic valve 3 closes to stop back flow of blood into the left ventricle 1. The left atrium 5 contracts to fill the left ventricle 1 with further blood in preparation for the next systole stage. During the diastole stage, the blood pressure within the aorta 2 reduces to what is termed the diastolic blood pressure. The reduced pressure at this stage causes the wall of the aorta 2 to recoil (relax), restoring it back to its original diameter, as depicted in broken lines in FIG. 3. The blood is accordingly pumped through the aorta and into the arteries in a pulsating manner.

The ability of the aorta 2 to expand and recoil during the systole and diastole stages is dependent upon the elasticity of the aorta wall which is a result of the elastin fibres present in the aorta wall.

Systolic blood pressure progressively increases with ageing that begins in childhood until the eighth or ninth decade, whereas diastolic blood pressure tends to remain constant in the fifth or sixth decade but decreases thereafter. Consequently, the pulse pressure, being the pressure differential between the systolic and diastolic blood pressure, increases with ageing. This form of hypertension is termed isolated systolic hypertension and increases in frequency with increasing age.

Various studies have shown that elevated systolic pressure is associated with a greater risk of heart failure, stroke, and acute myocardial infarction, and that treatment of elevated systolic pressure can delay or prevent such adverse events even when diastolic pressure is normal or low.

A number of studies have also shown that, in patients over 50, there is a stronger association between adverse cardiovascular (particularly coronary) events and pulse pressure, than systolic or diastolic pressure in isolation. Accordingly, for any given systolic pressure, the diastolic pressure is inversely related to the risk of adverse cardiovascular events, possibly due to reduction in coronary perfusion with decreased diastolic pressure.

Heart failure is reported to effect 2 to 5 percent of people in Western societies aged over 65, and 10 percent of those aged over 75. It is also reported to be the leading cause of hospital admission and readmission in Americans older than 65.

The increase in systolic blood pressure with age is largely a result of stiffening of the aorta and other large elastic arteries. Dilatation of the aorta/arteries is typically associated with this stiffening. The stiffening and dilatation is a result of the repetitive cyclic stress applied to the aorta wall during expansion and subsequent relaxation of the aorta. The cyclic stresses applied to the aorta wall result in fatigue, fracture and fragmentation of the elastin fibres which provide the aorta wall with its elasticity. The mechanical properties of the aorta wall gradually become dominated by inelastic collagen. The breakdown of the elastin fibres results in the aorta becoming inelastic and stiff, thereby losing its capability to restore to its original diameter after expansion during the systole stage. The aorta accordingly remains permanently dilated.

A young, healthy ascending aorta typically has an external diameter of the order of 25 mm when subjected to normal diastolic pressure of 70 mmHg (9.3 kPa), and a wall thickness of the order of 2 mm. The diameter and wall thickness decrease from the proximal portions of the aorta to the more distal portions. Dilatation of the aorta associated with aortic stiffening may result in an increase in the external diameter of the ascending aorta at diastolic pressure to as large as 40 mm or more.

Measurement of the stiffness of the aorta has been the subject of various studies, measuring various different stiffness related properties. The measurement of pure tensile stiffness of a section of aorta, providing a Young's modulus, is not readily obtained given the non-homogeneous nature of the aorta. A common, and more meaningful, stiffness measurement is the pressure-strain elastic modulus ($E_p$):

$$E_p = (dP/dD) \times D$$

where D=aortic diameter;
dD=change in aortic diameter;
dP=change in aortic pressure.

The aortic stiffness is non-linear, increasing with increasing pressure, partly due to the biochemical, structural and geometric makeup of the extracellular matrix of the aorta wall, and hence the aortic stiffness at a specified pressure is measured as the tangent to the pressure/diameter curve. Stiffness can most meaningfully be measured as the average stiffness over the range of pressures experienced during physiological flow as follows:

$$E_p = (dP/dD) \times D$$

where D=diastolic aortic diameter;
dD=pulsatile change in aortic diameter (systolic diameter minus diastolic diameter)
dP=pulse pressure (systolic pressure minus diastolic pressure)

This stiffness varies greatly from subject to subject, and increases from the proximal portions of the aorta to the more distal portions. A typical young, healthy ascending aorta will have a stiffness ($E_p$) of about $0.41 \times 10^6$ dyn/cm² (41 kPa). A stiffened ascending aorta may have an increased stiffness of up to $16 \times 10^6$ dyn/cm² (1600 kPa) or more.

Aortic stiffening alters the left ventricular systolic pressure in two ways. First, there is a greater rise in pressure at the time of peak aortic flow in the systole stage as a result of failure of the aorta to expand as blood is pumped from the left ventricle. Secondly, aortic stiffening increases the pulse wave velocity in the large blood vessels. This causes pressure waves reflected from peripheral sites to return to the aorta earlier than usual, boosting pressure in the late systole stage. This early return of the reflected wave to the ascending aorta during the ventricular ejection of systole is detrimental since systolic pressure and left ventricular afterload is increased. The early return of the reflected wave also reduces diastolic pressure and the capacity for myocardial perfusion. Each of these factors results in an increase in cardiac load of the left ventricle.

The most effective means of treating, or preventing, heart failure is to reduce cardiac load either pharmacologically or mechanically. Mechanical reduction of cardiac load using intra-aortic balloon counter pulsation and ventricular assist devices have proven effective. However, intra-aortic balloon counter pulsation can only be used as a temporary treatment. Ventricular assist devices are also expensive and temporary measures.

International Publication No. WO 2004/056274 A1 (the entire contents of which are incorporated herein by cross-reference) proposes an alternate means of treating, or preventing heart failure by reducing the effective stiffness of a stiffened and dilated blood vessel, particularly the aorta, by encasing a portion of the blood vessel with an elastic membrane that reduces the circumference of the blood vessel such that the membrane itself carries at least a substantial portion of the load placed on the vessel throughout diastole and systole, such that the effective stiffness of the encased portion of the blood vessel will be dictated by that of the elastic membrane. The membrane must, however, generally be applied to the blood vessel by wrapping a sheet form of the membrane about the vessel and securing it to the vessel, which can present various difficulties.

OBJECT OF THE INVENTION

It is an object of the present invention to overcome or substantially ameliorate at least one of the above disadvantages, or at least to provide a useful alternative to previously proposed methods and associated devices for treating stiffened blood vessels.

SUMMARY OF THE INVENTION

In a first aspect, the present invention provides a device for treating a stiffened blood vessel comprising a self-supporting, surgically implantable, elongate casing adapted to extend about and restrain a stiffened portion of the blood vessel, said casing defining an elongate cavity for receipt of the stiffened portion of the blood vessel, said cavity having a transverse cross-section with an aspect ratio of greater than one in an unloaded state, said casing being configured such that, upon application of increasing pressure to said casing from within said cavity, said casing elastically deforms such that said aspect ratio decreases towards one and the area of said cross-section increases.

Typically, said transverse cross-section of said cavity has an aspect ratio of 1.5 to 2.0 in the unloaded state.

In one embodiment, said casing is in the form of an elongate sleeve having an opening extending along its length, said cavity having an oval shaped transverse cross-section in said unloaded state, said casing comprising a pair of opposing first wall portions located at opposing ends of a major axis of said transverse cross-section and a pair of opposing second wall portions located at opposing ends of a minor axis of said transverse cross-section, wherein said first wall portions are each stiffer than said second wall portions.

Typically said opening extends along a length of one of said first wall portions.

In a preferred form, said casing is a unitary structure.

In one form, said first wall portions each have a greater thickness than said second wall portions. In such a form, said casing may be formed of a homogenous material.

In one form, said device further comprises a clip to close said opening.

In an alternate form, said sleeve may be configured such that said opening is self-closing when said casing is in said unloaded state and remains closed upon application of increasing pressure to said casing from within said cavity, at least up until a predetermined pressure.

The casing may longitudinally extend substantially linearly from end to end or alternatively may longitudinally extend in a curved manner.

Typically, said transverse cross-section is substantially constant along a length of said casing.

In a further embodiment, said casing comprises:

an elongate rigid first element having opposing first element edge portions; and an elongate elastically deformable second element having opposing second element edge portions secured or securable to said first element edge portions to define said cavity between said first and second elements, said aspect ratio of said cross-section being defined by a width of said first element between said first element edge portions, divided by a maximum distance between said first element and said second element.

In a preferred form, the interior wall portion of said cavity defined by said first element is substantially planar.

In another embodiment, said casing comprises a pair of opposing spring clips, each of said spring clips comprising:

a first arm extending from a first arm proximal end to a first arm distal end, and a second arm extending from a second' arm proximal end to a second arm distal end, said proximal first arm end being connected to said proximal second arm end and said distal first arm end being spaced from said distal second arm end to define a recess between said first and second arms for receipt of the stiffened portion of the blood vessel;

wherein said spring clips are adapted to extend partway around the stiffened portion of the blood vessel from opposing sides and said first arm distal ends of said spring clips attached to each other and said distal second arm ends of said spring clips attached to each other.

Typically, said arms of each of said clips are configured to overlap when in said unloaded state.

In a second aspect, the present invention provides a device for treating a stiffened artery comprising a self-supporting, surgically implantable, elongate casing adapted to extend about a stiffened portion of the artery, said casing being configured to restrain the stiffened portion of the artery, in use, to an oval cross-section during diastole and to elastically deform to allow the stiffened portion of the artery to expand into a more circular cross-section during systole.

In a third aspect, the present invention provides a method of treating a stiffened artery comprising:

extending an elongate casing about a stiffened portion of said artery so as to restrain said stiffened portion of said artery into an oval cross-section during diastole;

allowing said casing to elastically deform during systole, allowing said stiffened portion of said artery to expand into a more circular cross-section during systole.

Typically, said casing restrains said stiffened portion of said artery such that a circumference of said stiffened portion of said artery remains substantially constant throughout diastole and systole.

Typically said artery is the aorta, particularly the ascending aorta, aortic arch or descending thoracic aorta.

The stiffened portion of said artery may be a grafted synthetic portion of said artery. The grafted synthetic portion may be a woven polyester graft. Alternatively, the grafted synthetic portion may be a polytetrafluoroethylene or Gore-Tex® graft.

The stiffened portion of said artery may be in a dilated state prior to treatment.

BRIEF DESCRIPTION OF THE DRAWINGS

Preferred embodiments of the present invention will now be described, by way of example only, with reference to the accompanying drawings wherein:

FIG. 11 is a schematic perspective view of a form of the device of FIG. 7 suitable for treatment of the ascending aorta;

FIG. 12 is a schematic perspective view of a form of the device of FIG. 7 suitable for treatment of the aortic arch;

FIG. 13 is a schematic front elevation view of the descending thoracic aorta treated with multiple devices of FIG. 7;

DETAILED DESCRIPTION OF THE PREFERRED EMBODIMENTS

Whilst the method of treatment proposed in International Publication No. WO 2004/056274 involves encasing a stiffened and dilated blood vessel with a membrane to maintain a circular shaped cross-section of the blood vessel but reduce its diameter to one approximating that of a healthy blood vessel throughout systole and diastole, preferred embodiments of the present invention utilise an alternate methodology of changing the shape of the blood vessel so as to reduce its cross-sectional area in diastole and allow an increase in cross-sectional area in systole.

Figure 1:
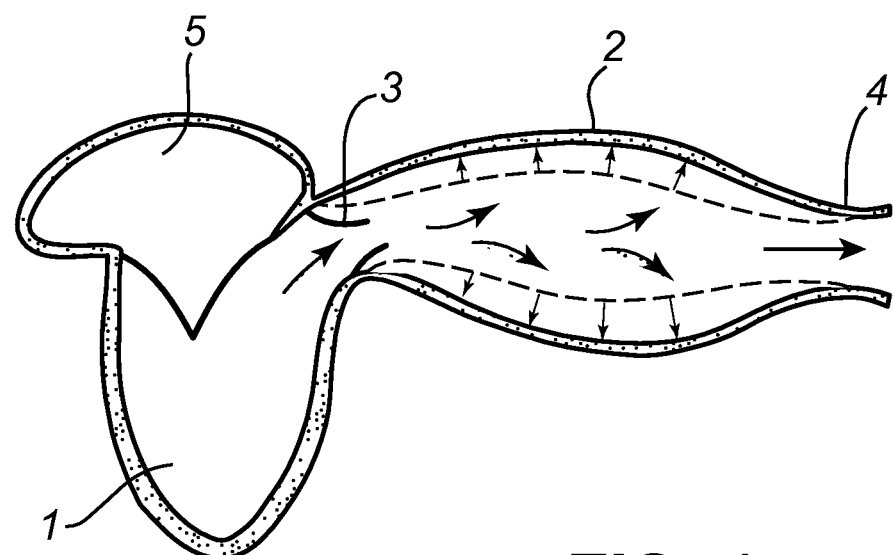
FIG. 1 is a schematic longitudinal partial cross-sectional view of a heart and aorta in systole.
Figure 2:
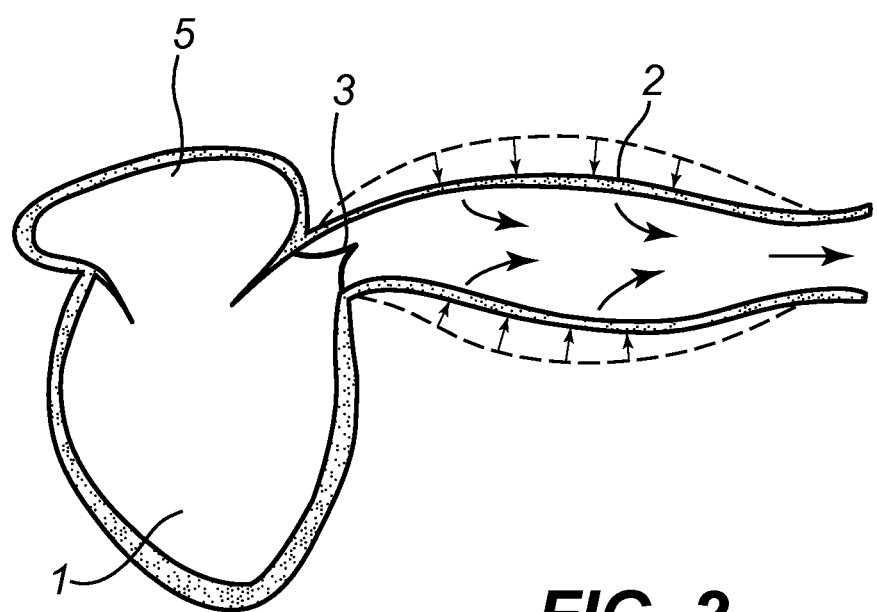
FIG. 2 is a schematic longitudinal partial cross-sectional view of the heart and aorta of FIG. 1 in diastole.
Figure 3:
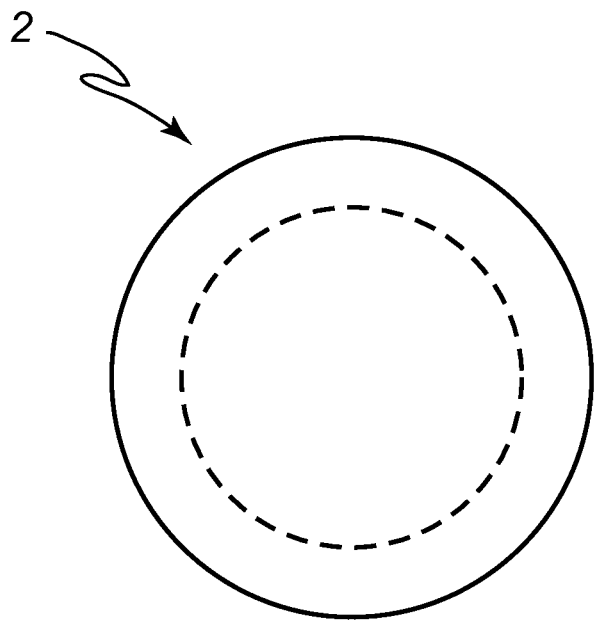
FIG. 3 is a schematic transverse cross-sectional end view of the aorta of FIG. 1 depicted both in systole (shown as a continuous line) and diastole (shown as broken lines)
Figure 4:
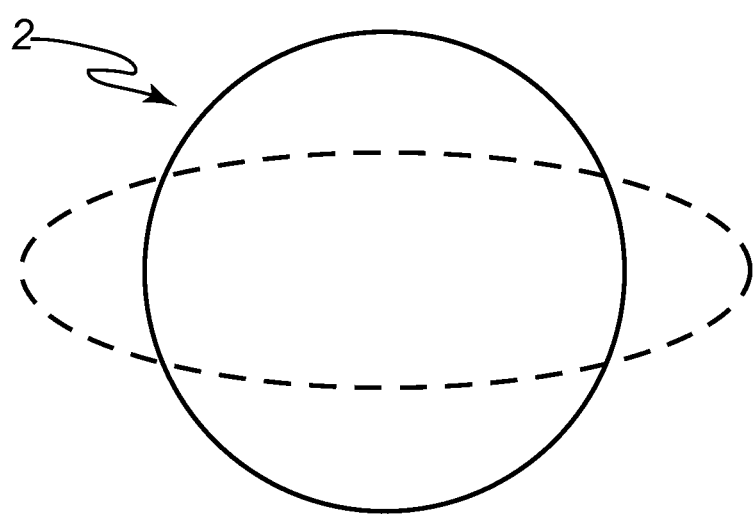
FIG. 4 is a schematic transverse cross-sectional end view of a stiffened aorta depicted both in systole (shown as a continuous line) and diastole (shown as broken lines) after treatment according to a preferred embodiment.

FIG. 4 depicts a stiffened portion of artery, particularly a stiffened aorta portion 2, that has been treated with a method according to at least a preferred embodiment. FIG. 4 depicts the treated stiffened aorta portion 2 in diastole (in broken lines) and in systole (in a continuous line). As will be discussed in further detail below, the stiffened aorta portion 2 is restrained by an elongate casing (not depicted in FIG. 4) extending about the stiffened aorta portion 2 to restrain the stiffened aorta portion 2 into a generally oval cross-section during diastole. As pressure within the stiffened aorta portion 2 increases during systole, the casing is allowed to elastically deform (under action of the pressure in the stiffened aorta portion 2) in a manner which allows the stiffened aorta portion 2 to expand into a more circular cross-section during systole as depicted in FIG. 4. In particular, in the configuration of FIG. 4, the stiffened aorta portion 2 is shown to obtain a fully circular cross-section during systole. It can be readily appreciated from FIG. 4 that the cross-sectional area of the stiffened aorta portion 2 increases significantly due to the changing shape from generally oval towards circular, without a significant increase in the circumference of the stiffened aorta portion 2, such that there is little or no tensile extension of the aorta wall. This change in cross-sectional area can be made to replicate that of a healthy aorta, as depicted in FIG. 3. The casing carries a substantial portion of the cardiac loads acting on the stiffened aorta portion throughout systole and diastole.

Figure 5:
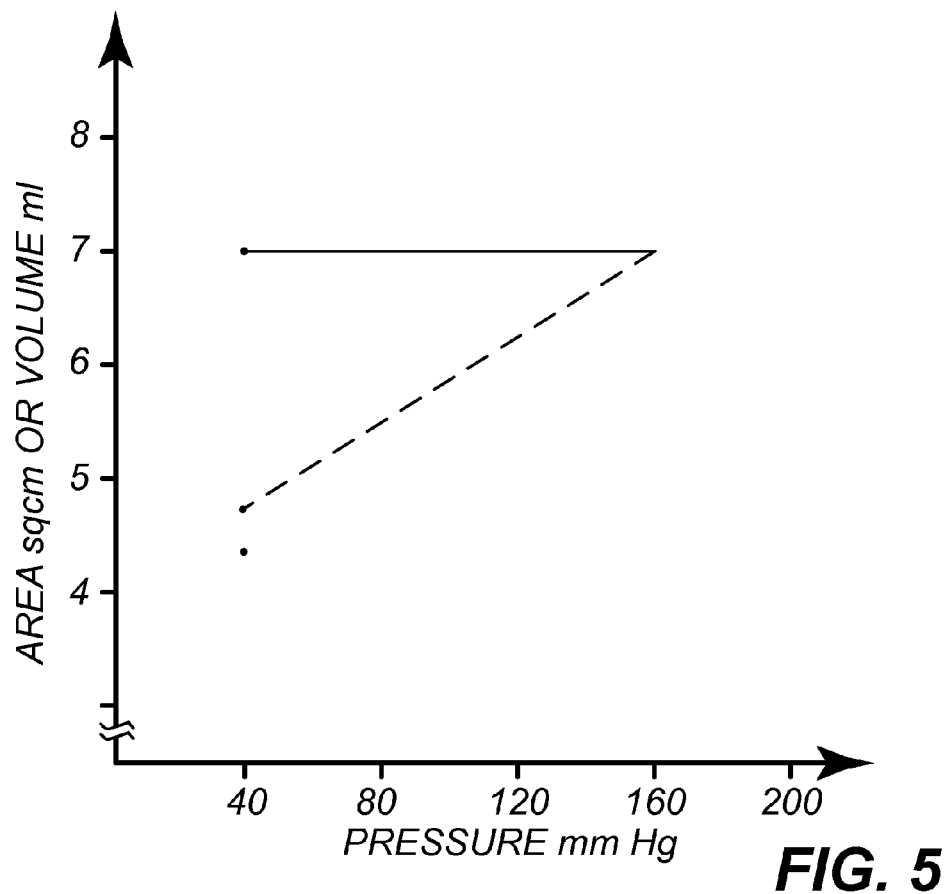
FIG. 5 is a graph depicting the aortic cross-sectional area variation over the cardiac cycle of a stiffened aorta before and after treatment according to the method of a preferred embodiment.

FIG. 5 depicts a calculated comparison of the change in cross-sectional area of a stiffened aorta portion 2, both before (in a continuous line) and after treatment (in broken lines) according to a preferred embodiment. FIG. 5 depicts this change in cross-sectional area throughout the pressure range experienced in a cardiac cycle of the stiffened aorta portion 2 prior to treatment, from a minimum pressure during diastole of approximately 40 mmHg (5.3 kPa) to a maximum pressure during systole of approximately 160 mmHg (21.3 kPa). In the example depicted, the untreated stiffened aorta portion 2 has an internal diameter of 30.0 mm at the minimum pressure during diastole and, due to the stiffened-nonelastic nature of the stiffened aorta portion 2, a maximum diameter of only 30.5 mm at the maximum pressure during systole. This provides a small 1.7% increase in diameter of the stiffened aorta portion 2 and a small 3.3% increase in internal cross-sectional area from 707 mm² to 730 mm² Following treatment according to the method of the preferred embodiment, however, the internal cross-sectional area of the stiffened aorta portion 2 increases from an initially reduced area of 471 mm² to an area of 707 mm² at the highest pressure, equivalent to that experienced during systole of the untreated aorta portion 2 (although this high pressure would not be encountered following treatment), without changing the initial circumference of 94.2 mm of the stiffened aorta portion 2. This provides a cross-sectional area increase of 236 mm², or approximately 50%.

Figure 6:
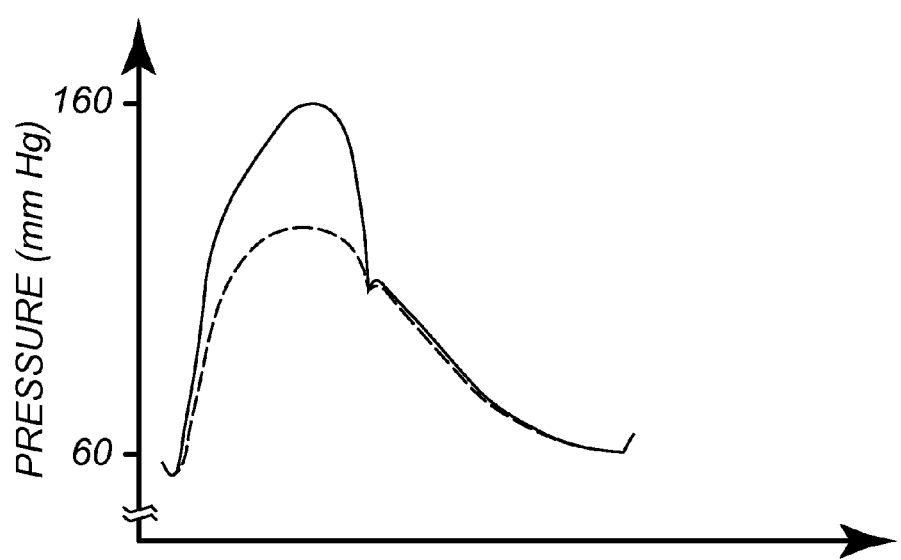
FIG. 6 is a graph depicting the aortic pressure range contour over the cardiac cycle for a stiffened aorta before and after treatment according to the method of a preferred embodiment.

This significant increase in cross-sectional area during systole increases the effective compliance (i.e., decreases the effective stiffness) of the stiffened aorta portion 2, decreasing the pressure rise in the stiffened aorta portion 2 for ejection of the same amount of blood from the ventricle. This results in decreased aortic systolic and pulse pressure as represented in FIG. 6, which depicts the aortic pressure wave contour of the stiffened aorta portion 2 before (in a continuous line) and after treatment (in broken lines). This decrease will also reduce left ventricular load and coronary blood flow requirements. Pulsatile pressure and flow in small brain and kidney micro-vessels will also decrease, reducing potential damage to these vessels and in the organs they supply that may otherwise occur as a result of aortic stiffening.

Figure 7:
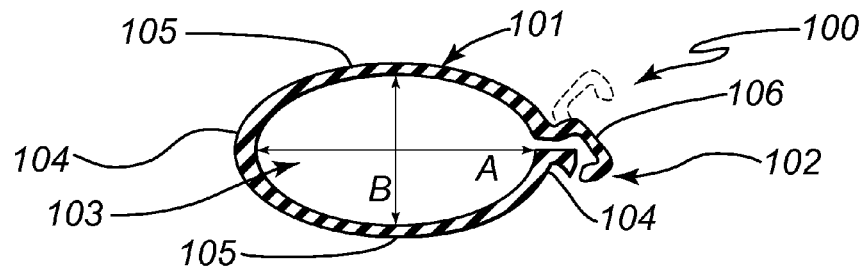
FIG. 7 is a schematic end elevation view of a device for treating a stiffened blood vessel according to a first embodiment.
Figure 8:
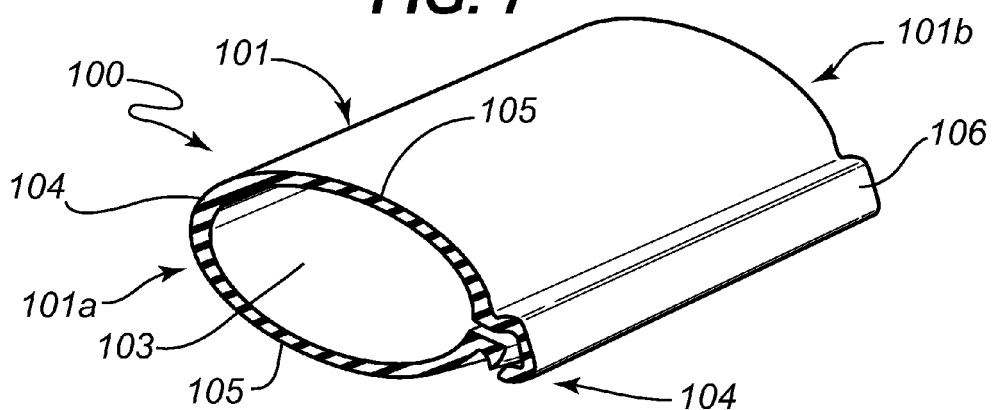
FIG. 8 is a schematic perspective view of the device of FIG. 7.

A suitable device 100, according to a first embodiment, for carrying out this method is depicted in FIGS. 7 through 10. The device 100 comprises a self-supporting, surgically implantable, elongate casing 101 that longitudinally extends between opposing casing ends 101a, 101b. The casing 101 is adapted to extend about and restrain a stiffened portion of a blood vessel, particularly an artery, such as a stiffened aorta portion 2. The casing 101 is here specifically a unitary structure in the form of an elongate sleeve which has an opening 102 extending along its length between the opposing casing ends 101a, 101b. The casing 101 defines an elongate cavity 103 for receipt of the stiffened aorta portion 2. The cavity 103 has a transverse cross-section with an aspect ratio that is here defined by the maximum width of the cavity 103, measured along a major axis A of the cross-section, divided by the maximum height of the cross-section, measured along a minor axis B of the cross-section that is orthogonal to the major axis A. In the unloaded state, as depicted in FIG. 7, the aspect ratio is greater than 1, and typically 1.5 to 2.0, with the cross-section particularly being an oval-shaped cross-section in this particular embodiment.

The casing 101 comprises a pair of opposing first wall portions 104 located at opposing ends of the major axis A and a pair of opposing second wall portions 105 located at opposing ends of the minor axis B. The first wall portions 104 are separated by the width of the cavity cross-section and can be seen to each be bent through a relatively tight radius compared to the flatter second wall portions 105 which are separated by the smaller height of the cavity cross-section.

Figure 9:
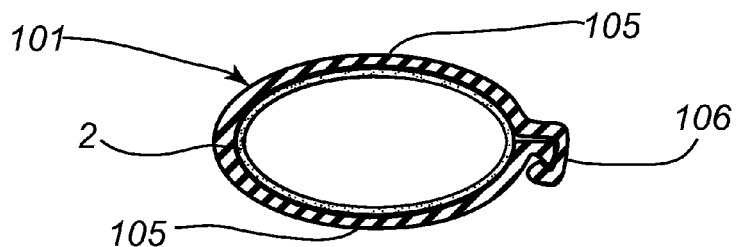
FIG. 9 is a schematic cross-sectional view of a stiffened aorta, encased with the device of FIG. 7, during diastole.
Figure 10:
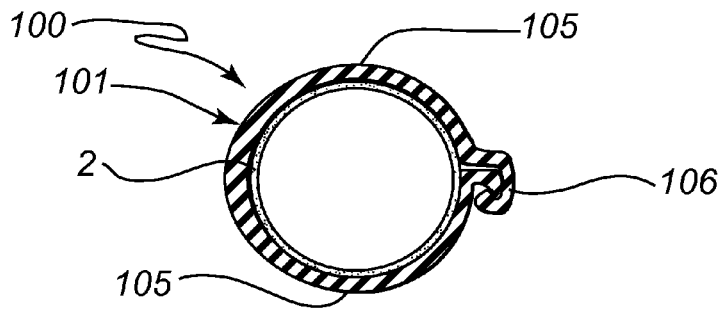
FIG. 10 is a schematic cross-sectional view of a stiffened aorta, encased with the device of FIG. 7, during systole.

Referring to FIGS. 9 and 10, the casing 101 is configured such that, upon application of increasing pressure to the casing 101 from within the cavity 103, the casing 101 elastically deforms such that the aspect ratio decreases towards 1 and the cross-sectional area of the cavity 103 increases. The casing 101 is particularly configured to restrain the stiffened aorta portion 2 to a generally oval cross-section during diastole, as depicted in FIG. 9, and to elastically deform to allow the stiffened aorta portion 2 to expand into a more circular cross-section during systole, as depicted in FIG. 10. The casing 101 restrains the stiffened aorta portion 2 into the flattened generally oval-shaped cross-section during diastole by compressing opposing sides of the stiffened aorta portion 2 between the second wall portions 105. Increasing pressure within the stiffened aorta portion 2 during systole acts primarily on the second wall portions 105.

To provide the desired shape change of both the casing 101 and the stiffened aorta portion 2 restrained therein, the first wall portions 104 are each stiffer than the second wall portions 105. This will typically be achieved by forming the first wall portions 104 with a greater thickness than the second wall portions 105, particularly where the casing 101 is formed of a homogenous material. It is also envisaged, however, that the wall portions of the casing 101 may be of a constant thickness with the increased stiffness of the first wall portions 104 being provided by reinforcing or otherwise being formed of a stiffer material.

The casing 101 may be formed of any suitable surgically implantable (biologically compatible) material capable of elastic deformation over multiple cycles (typically up to at least 30×10⁶ per year) and which can be preformed to be self-supporting. Suitable materials include stainless steel, titanium, nickel titanium alloy, including NITINOL (NIckel TItanium Naval Ordinance Laboratory). Other possible materials include polymers and biologically modified or engineered materials. The casing 101 may have a stent-like frame form, or may have a continuous form. If the casing 101 is formed of a metallic material, it is preferred that the material be non-magnetic so that magnetic resonance imaging techniques can be used subsequently. The casing ends 101a, 101b will preferably be formed of a softer material, so as to minimise erosion of the adjacent portion of the artery being treated, and/or other adjacent structures such as intercostal arteries.

As noted above, the casing 101 is preformed so as to be self-supporting, providing the desired shape discussed above when in the unloaded state. The casing 101 may be formed such that the opening 102 remains closed, or at least almost closed, both in diastole and when increasing pressure is applied by the stiffened aorta portion 2 during systole. Alternatively, the device 100 may include a clip 106 for securing the opening 102 closed after the casing 101 has been applied to a stiffened portion of blood vessel to be treated. Such a clip 106 may take any of various forms, and will generally have one end secured to an edge region of one of the first wall portions 104 on one side of the opening 102, and securable to an opposing edge region of the first wall portion 104 on the opposing side of the opening 102. In this regard, the outer face of the second edge region of the first wall portion 104 may be formed with an elongate recess or other form of interlocking structure to interlock with the distal end of the clip 106.

The casing 101 may be applied to a stiffened portion of blood vessel to be treated by first prising open the casing 101 to allow the stiffened portion of blood vessel to pass laterally into the cavity 103 through the opening 102 as the casing 101 is extended over the stiffened portion of blood vessel. After releasing the casing 101, the preformed self-supporting nature of the casing 101 will result in it closing back over the stiffened portion of blood vessel, restraining the blood vessel in the manner discussed above. For configurations including a clip 106, the clip 106 will secure the opening 102 closed after extending the casing 101 over the stiffened portion of blood vessel. Rather than having the casing 101 extend about the entire circumference of the stiffened portion of blood vessel, with the opening 102 being closed following application, it is also envisaged that the casing 101 might only extend partway about the circumference of the stiffened portion of blood vessel. The casing 101 would generally extend about at least a majority of the circumference of the stiffened portion of blood vessel so that adequate compressive load could be applied to the opposing sides of the stiffened portion of blood vessel to allow it to be restrained in the manner described above.

The casing 101 will preferably be applied to the ascending aorta, aortic arch and proximal descending thoracic aorta, given that these arteries normally account for about 70% of the cushioning function of the arterial tree. These arteries also show the greatest degree of stiffening and dilatation with age. Such degeneration is attributable to multiple (two billion in 50 years) cycles of strain with each cardiac cycle, resulting in fatigue and fracture of elastin fibres in the aortic wall, so that stresses are then transferred to stiffer collagen fibres.

The casing 101 may longitudinally extend substantially linearly between the casing ends 101a, 101b, or alternatively may longitudinally extend in a curved manner to suit a specific application. Similarly, the transverse cross-section of the cavity 103 may be substantially constant along the length of the casing 101, however the cross-section may also vary to suit the particular artery to which it is to be applied.

For example, referring to FIG. 11, a specific form of the casing 101 is depicted that is particularly suitable for application to the ascending aorta, having a preformed curve that generally matches that of the ascending aorta and a transverse cross-section that tapers slightly towards the end 101b of the casing 101 that is to be located adjacent the aortic arch. Another curved form of the casing 101 is depicted in FIG. 12, with this casing 101 being provided with a series of cut-outs 107 in its radially outer wall to enable the brachiocephalic artery, left common carotid artery and left subclavian artery to extend through the casing 101. Slits 108 are provided in one side wall of the casing 101, joining each cut-out 107 with the opening 102 that is here formed on the radially inner wall of the casing 101, allowing the casing 101 to be located on one side of the aortic arch.

Referring next to FIG. 13, application of multiple short casings 101 to the descending thoracic aorta 6 is depicted. Each casing 101 is applied to a short portion of the descending thoracic aorta between intercostal arteries 7 which branch off the descending thoracic aorta 6.

For patients undergoing coronary artery bypass grafting, one or more casings 101 may be applied to the ascending aorta and proximal arch of the aorta through the median sternotomy wound created during the bypass procedure. One or more casings 101 can also be applied to the distal arch and ascending thoracic aorta through a left thoracotomy or left thoracoscopic technique leaving intercostal arteries intact.

The treatment may also be undertaken on patients undergoing other forms of cardiac surgery such as valve repair or replacement, or replacement of the aortic root or ascending aorta. The treatment is also suitable for being carried out on patients undergoing thoracic surgery such as pneumonectomy, lobectomy or excision of carcinoma or any other surgical procedure where there is a risk of precipitating acute heart failure in a patient with impaired left ventricular function when aortic dilatation and stiffening are present. The treatment may also be used as a primary treatment of isolated systolic hypertension. The treatment may also be used as a primary treatment of heart failure when aortic dilatation and stiffness are present.

When the treatment is carried out during surgery where median sternotomy is not performed, the ascending aorta and arch of the aorta can be accessed through a right thoracotomy, right thoracoscopic procedure or minimal access surgery.

As well as utilising the casing 101 to treat the aorta, the technique is also expected to be useful in treating similar stiffness and dilatation in the major arteries.

Whilst it is envisaged that the treatment will be suitable as a long term solution for many patients suffering cardiac failure or other problems associated with aortic stiffening, the present treatment may also be utilised as a short term solution for patients awaiting the supply of a replacement heart for heart transplant surgery. The treatment is also expected to be suitable for a short term solution to improve the cardiovascular function and strength of patients requiring coronary bypass surgery but who are perceived to be too weak to be subjected to such surgery. For such patients, a three to six month period following aortic treatment as described herein may be sufficient to prepare the patient for primary bypass surgery. The treatment is also expected to be suitable for a short term solution to improve myocardial perfusion in acute coronary syndromes to improve the cardiovascular function and strength of patients requiring myocardial revascularisation (coronary artery bypass grafting, coronary angioplasty and coronary stenting). For such patients a 3 day to 1 month period following aortic treatment with the casing 101 may be sufficient to prepare the patient for revascularisation.

Such treatments may be conducted through minimally invasive thoracoscopic techniques.

The casing 101 can also be applied percutaneously to the outside of the aorta.

The casing 101 may also be applied to a grafted synthetic portion of a blood vessel, particularly a grafted synthetic aortic portion. Such grafts are typically formed of a stiff woven polyester material, Gore-Tex® fabric or polytetrafluoroethylene. The stiffened nature of such grafts results in them benefitting from the present method to achieve the desired arterial compliance.

Figure 14:
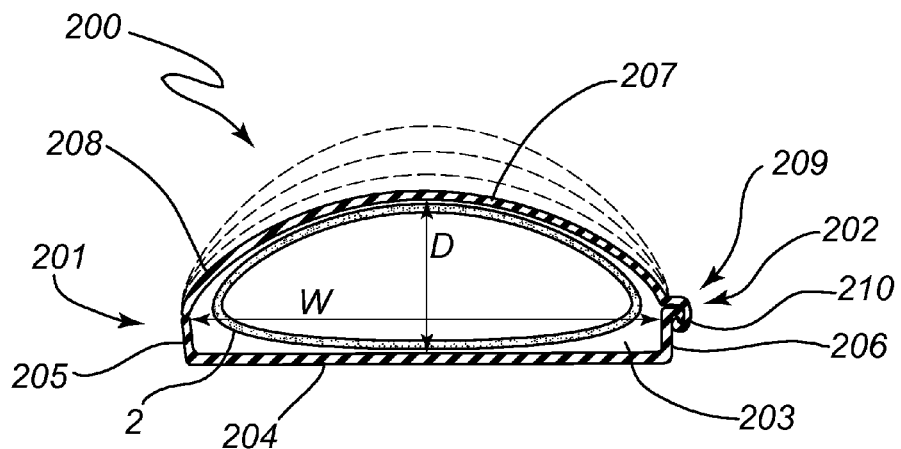
FIG. 14 is a schematic transverse cross-sectional view of a device for treating a stiffened blood vessel according to a second embodiment.
Figure 15:
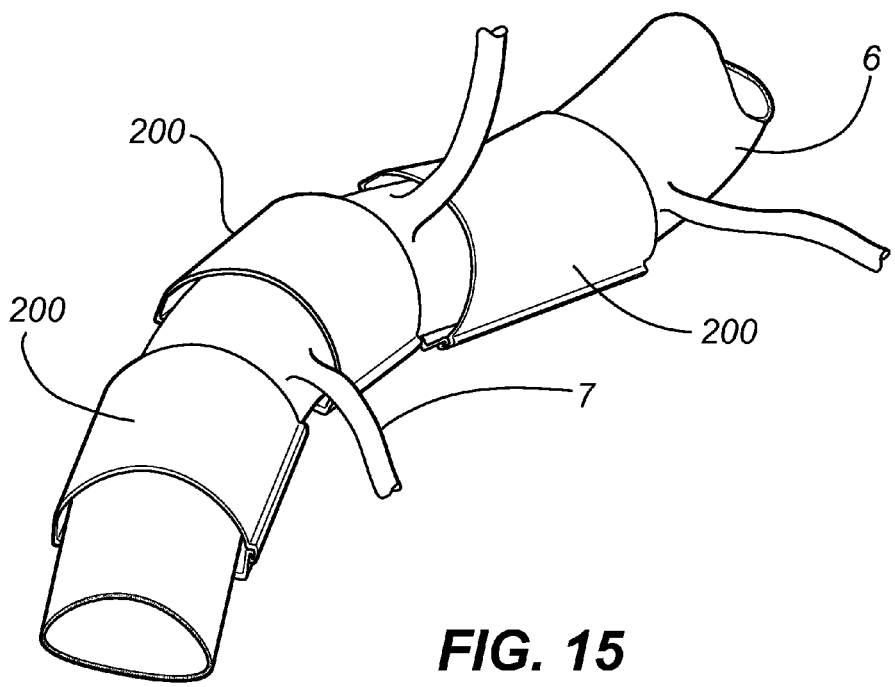
FIG. 15 is a schematic front elevation view of the descending thoracic aorta having applied thereto the device of FIG. 14.

A device 200 according to a second embodiment, for carrying out the method of the preferred embodiment is depicted in FIGS. 14 and 15.

The device 200 comprises an elongate casing 201 formed of an elongate rigid first element 204 having opposing first element edge portions 205, 206 and an elongate elastically deformable second element 207 having opposing second element edge portions 208, 209 that are secured (or at least securable) to the first element edge portions 205, 206 so as to define a cavity 203 extending along the length of the casing 201.

In the arrangement depicted, the first element edge portion 205 is permanently secured to the second element edge portion 208, whilst the first element edge portion 206 is releasably securable to the second element edge portion 209, thereby defining a closable opening 202 that extends along the length of the casing 201, enabling the casing 201 to be extended about a stiffened portion of a stiffened blood vessel, such as a stiffened portion of the descending thoracic aorta 6, as depicted in FIG. 15. The second element edge portion 209 may be secured to the first element edge portion 206 by way of a clip or other inter-engaging locking structure 210 either integrally formed with, or secured to, the edge portions 209, 206. It is also envisaged that the second element edge portion 208 may be releasably secured to the first element edge portion 205 in a similar manner such that the second element 207 may be completely removed from the first element 204, allowing the first element 204 to first be positioned behind the stiffened portion of blood vessel to be treated with the second element 205 then extending across the opposing face of the stiffened portion of blood vessel and secured to the first element 204.

The cavity 203 has a transverse cross-section with an aspect ratio defined by a width W of the first element 204 between the first element edge portions 205, 206 divided by a maximum distance D between the first element 204 and the second element 207. In the unloaded state, this aspect ratio is greater than 1, typically being between 1.5 and 2.0. As represented in FIG. 14 depicting elastic deformation of the second element 207 as pressure within the cavity 203 increases during systole, this aspect ratio decreases towards 1 with increasing pressure. The first and second elements 204, 207 restrain the stiffened aorta portion 2 in a similar manner to that described above in relation to the device 100 of the first embodiment, initially restraining the stiffened aorta portion 2 to a generally oval-shaped cross-section during diastole. Then, by elastic deformation of the second element 207, resulting from the increasing pressure in the stiffened portion 2 acting on the first and second elements 204, 207 the stiffened aorta portion 2 is allowed to expand towards a more circular configuration.

The device 200 of the second embodiment is particularly suitable for applications where the rigid first element 204 may be located over a solid material, such as the thoracic spine.

Expansion of the casing 201, and stiffened aorta portion 2, will then primarily occur on the opposing side of the stiffened aorta portion 2 which would generally be in contact with softer structures (such as the trachea, oesophagus, pericardium and/or vena cava). These softer structures can be deformed or moved with each beat of the heart. This particular construction will also generally apply less force to the intercostal arteries 4 between each casing 201, and so provide less risk of their damage or rupture.

Figure 16:
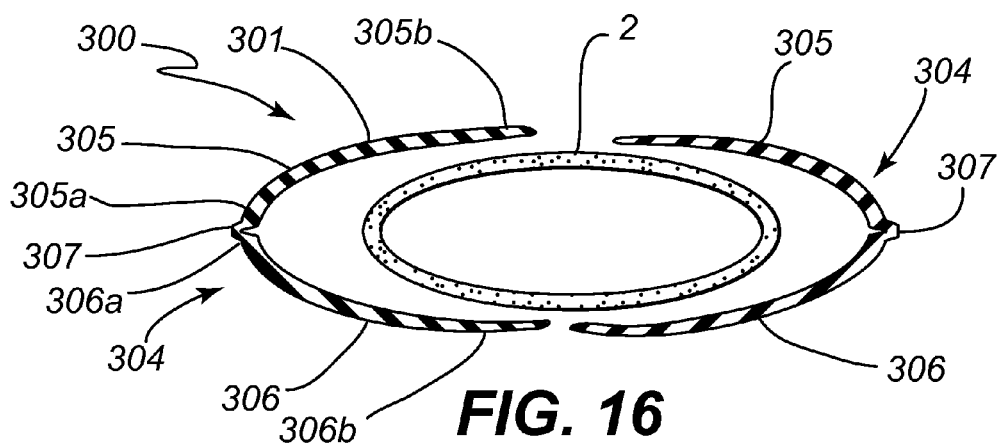
FIG. 16 is a schematic transverse cross-sectional view of a device for treating a stiffened blood vessel according to a third embodiment during implantation.
Figure 17:
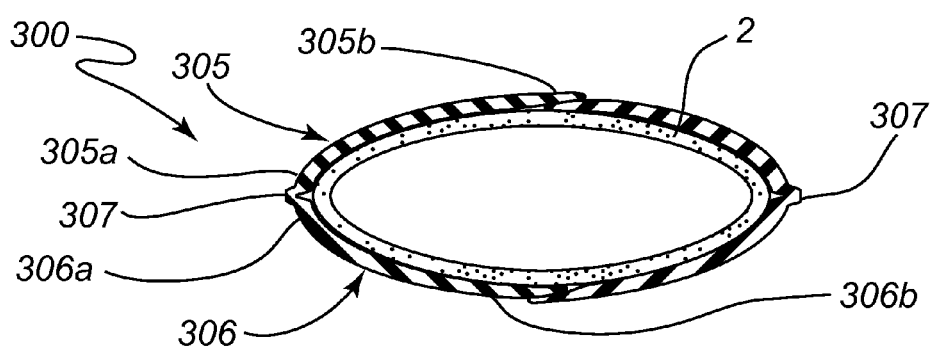
FIG. 17 is a schematic transverse cross-sectional view of the device of FIG. 16 encasing the aorta during diastole.
Figure 18:
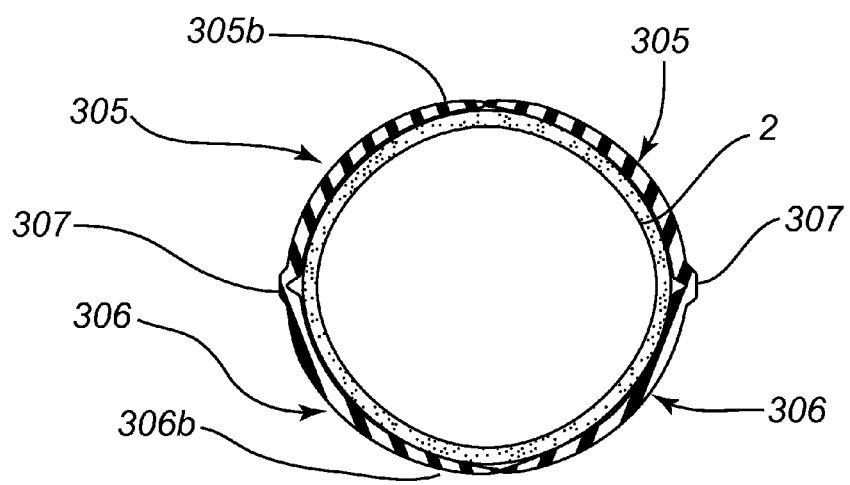
FIG. 18 is a schematic transverse cross-sectional view of the device of FIG. 16 encasing the aorta during systole.

A device 300 according to a third embodiment, for carrying out the method of the preferred embodiment, is depicted in FIGS. 16 through 18. The device 300 is in the form of a self-supporting, surgically implantable elongate casing 301 that comprises a pair of opposing spring clips 304.

Each of the spring clips 304 comprises a first arm 305 extending from a first arm proximal end 305a to a first arm distal 305b and a second arm 306 that extends from a second arm proximal end 306a to a second arm distal end 306b. The first and second arms 305, 306 extend between the opposing longitudinal ends of the casing 301. The first and second arms 305, 306 are connected to each other at or adjacent the first arm proximal end 305a and second arm 306a. In an unloaded state, as depicted in FIG. 16, each spring clip 304 defines a generally half oval-shaped cross-section recess, with the first and second arm distal ends 305b, 306b separated to enable the spring clip 304 to be extended partway over a stiffened aorta portion 2.

The stiffened aorta portion 2 may be treated by extending the two spring clips 304 over the stiffened aorta portion 2 from opposing sides and attaching the first arm distal ends 305b of the two spring clips 304 together and also attaching the second arm distal ends 306b together so as to close the opening between the spring clips 304. The respective arm distal ends 305b, 306b may be attached by way of separate adjustable fasteners or interlocking structures which still enable relative displacement of the arms of each spring clip 304. The arms will typically overlap, as depicted in FIG. 17, when subjected to low pressure during diastole, with increasing pressure during systole, as depicted in FIG. 18, decreasing the overlap between the arms as the stiffened aorta portion 2 and spring clips 304 expand.

To further provide for the expansion of the spring clips 304, the arms 305, 306 will typically be formed of an elastically deformable material. Suitable materials include stainless steel, titanium and nickel titanium alloys such as NITINOL. The first and second arm proximal portions 305a, 306a will typically be connected by a hinge mechanism 307 which either may be separately formed to and secured to the first and second arm proximal portions 305a, 306a, or as per the arrangement depicted in FIG. 16 may be integrally formed with the first and second arms 305, 306 such that each spring clip 304 is formed as a unitary structure.

The first and second arms 305, 306 of each spring clip 304 will preferably overlap, as depicted in FIG. 17, in a manner providing a smooth surface in contact with the stiffened aorta portion to prevent damage thereto. To further limit the possibility of damage to the stiffened aorta portion 2, the spring clips 304 may be separated from the stiffened aorta portion 2 with soft biocompatible material so as to prevent abrasion. The first and second distal ends 305b, 306b of each spring clip 304 and the surfaces at the end of the casing 301 will also typically be smooth and round to prevent abrasion and wear.

As best represented in FIG. 17, as with the devices 100, 200 of the first and second embodiments described above, the casing 301 of the device 300 effectively restrains the stiffened aorta portion 2 into a generally oval-shaped cross-section during diastole and expands from a low aspect ratio cross-section (of less than 1) towards an aspect ratio of 1 during systole, allowing the stiffened aorta portion 2 to take on a more circular cross-section in the same general manner as described above. This elastic deformation of the spring clip 304 is provided in the particular arrangement depicted by virtue of the hinge mechanisms 307, elastic deformability of the first and second arms 305, 306 and the adjustable attachment between the arm distal portions 305b, 306b of the two opposing spring clips 304.

The invention claimed is:

1. A method of treating a stiffened artery comprising:
    extending an elongate casing around an exterior of a stiffened portion of said artery so as to deform and restrain said stiffened portion of said artery into an oval transverse cross-section during diastole;
    allowing said casing to elastically deform during systole, allowing said stiffened portion of said artery to expand into a more circular transverse cross-section during systole;
    wherein said casing restrains said stiffened portion of said artery such that a circumference of said stiffened portion of said artery remains substantially constant throughout diastole and systole.

2. The method of claim 1, wherein said artery is the aorta.

3. The method of claim 1, wherein the stiffened portion of said artery is a grafted synthetic portion of said artery.

4. The method of claim 1, wherein the stiffened portion of said artery is in a dilated state prior to treatment.

5. A method of improving blood flow through a stiffened blood vessel by surgically implanting an elongate self-supporting casing around the blood vessel, the method comprising:
    extending the casing around an exterior of the blood vessel, the casing having a cavity;
    receiving the blood vessel in the cavity of the casing; wherein the cavity has a transverse cross-sectional area with an aspect ratio greater than one in a first configuration under diastolic blood pressure;

deforming and restraining the blood vessel into an oval transverse cross-section during diastole;

expanding the blood vessel into a more circular transverse cross-section during systole; and elastically deforming the casing during systole such that the aspect ratio of the cavity decreases towards one and the transverse cross-sectional area increases in a second configuration under systolic blood pressure to improve blood flow post implantation;

wherein said casing restrains said stiffened portion of said artery such that a circumference of said stiffened portion of said artery remains substantially constant throughout diastole and systole.

6. A method of treating a stiffened blood vessel by surgically implanting an elongate self-supporting casing around the blood vessel, the method comprising:

extending said casing around an exterior of a stiffened portion of said blood vessel such that said stiffened portion of said blood vessel is received in a cavity of said casing and is deformed and restrained by said casing into a transverse cross section having an aspect ratio of greater than one during diastole; wherein said cavity has a transverse cross-section with an aspect ratio greater than one when in an unloaded state; and elastically deforming said casing on application of increasing pressure to said casing on expansion of said stiffened portion during systole, such that the aspect ratios of said cavity and of said stiffened portion of said blood vessel each decrease towards one during systole and the area of said transverse cross-section of said cavity increases during systole;

wherein said casing restrains said stiffened portion of said artery such that a circumference of said stiffened portion of said artery remains substantially constant throughout diastole and systole.

7. The method of claim 1, further comprising:

securing the elongate casing around the stiffened artery with at least one spring clip, the at least one spring clip adapted to extend partway around the stiffened portion of the artery from opposing sides.

8. A method of treating a stiffened artery comprising:

extending an elongate casing around an exterior of a stiffened portion of said artery so as to deform and restrain said stiffened portion of said artery into an oval transverse cross-section during diastole;

allowing said casing to elastically deform during systole, allowing said stiffened portion of said artery to expand into a more circular transverse cross-section during systole without substantially changing the initial circumference of the stiffened portion of said artery.

9. A method of treating a stiffened artery comprising:

extending an elongate casing around an exterior of a stiffened portion of said artery so as to deform and restrain said stiffened portion of said artery into an oval transverse cross-section during diastole;

allowing said casing to elastically deform during systole, allowing said stiffened portion of said artery to expand into a more circular transverse cross-section during systole to provide a cross-sectional area increase of approximately 50 percent.

* * * * *